US012109035B2

(12) United States Patent
Mountford et al.

(10) Patent No.: US 12,109,035 B2
(45) Date of Patent: Oct. 8, 2024

(54) SYSTEM AND METHOD FOR TREATING AND MONITORING POST TRAUMATIC STRESS DISORDER (PTSD)

(71) Applicant: Translational Research Institute Pty Ltd as trustee for Translational Research Institute Trust, Woolloongabba (AU)

(72) Inventors: Carolyn Mountford, East Ryde (AU); David Crompton, Highfields (AU); Nathan Tosh, Mount Lofty (AU); Rosanna Tremewan, Camp Hill (AU)

(73) Assignee: DatChem, Brisbane (AU)

(*) Notice: Subject to any disclaimer, the term of this patent is extended or adjusted under 35 U.S.C. 154(b) by 812 days.

(21) Appl. No.: 16/791,797

(22) Filed: Feb. 14, 2020

(65) Prior Publication Data
US 2020/0261012 A1 Aug. 20, 2020

Related U.S. Application Data

(60) Provisional application No. 62/806,400, filed on Feb. 15, 2019.

(51) Int. Cl.
A61B 5/00 (2006.01)
A61B 5/05 (2021.01)
(Continued)

(52) U.S. Cl.
CPC ............ *A61B 5/4076* (2013.01); *A61B 5/374* (2021.01); *A61N 2/006* (2013.01)

(58) Field of Classification Search
CPC ........ A61B 5/4076; A61B 5/048; A61N 2/006
See application file for complete search history.

(56) References Cited

U.S. PATENT DOCUMENTS

2009/0024786 A1 1/2009 Chan et al.
2012/0116149 A1* 5/2012 Pilla .................... A61N 1/36025
600/14
(Continued)

FOREIGN PATENT DOCUMENTS

WO WO-2010066000 A1 * 6/2010 ......... G01N 33/6896
WO WO-2017042635 A1 * 3/2017 ............. A61B 5/055

OTHER PUBLICATIONS

Henigsberg, N. et al. "Changes in Brain Metabolites Measured with Magnetic Resonance Spectroscopy in Antidepressant Responders with Comorbid Major Depression and Posttraumatic Stress Disorder." Collegium Antropologicum, 2011, vol. 35, Suppl. (1), pp. 145-148. (Year: 2011).*

(Continued)

Primary Examiner — Thaddeus B Cox
Assistant Examiner — Joshua Daryl D Lannu
(74) Attorney, Agent, or Firm — Lucas & Mercanti, LLP

(57) ABSTRACT

A method and system for monitoring therapeutic interventions for treating a patient with PTSD comprises using a scanner to obtain pre-treatment neural spectroscopic data of at least one neuromarker chemical in the brain of the patient before treatment, treating the patient with at least one treatment protocol, after treatment, obtaining post-treatment neural spectroscopic data of the at least one neuromarker chemical in the brain of the patient, and comparing the results of the pre-treatment and post-treatment data to enable a determination of the effectiveness of the treatment.

19 Claims, 6 Drawing Sheets

(51) Int. Cl.

| | |
|---|---|
| *A61B 5/055* | (2006.01) |
| *A61B 5/16* | (2006.01) |
| *A61B 5/374* | (2021.01) |
| *A61M 21/00* | (2006.01) |
| *A61N 2/00* | (2006.01) |
| *A61N 2/02* | (2006.01) |
| *G01R 33/46* | (2006.01) |
| *G16H 20/70* | (2018.01) |

(56) References Cited

U.S. PATENT DOCUMENTS

2014/0058189 A1* 2/2014 Stubbeman ............ G16H 20/10
  600/13
2017/0365101 A1* 12/2017 Samec ................ G02B 27/017

OTHER PUBLICATIONS

Written Opinion of the International Searching Authority; PCT/IB2020/051284; May 26, 2020 (7 pages).

International Search Report; PCT/IB2020/051284; May 26, 2020 (5 pages).

Ham, B-J. et al. "Decreased N-acetyl-aspartate levels in anterior cingulate and hippocampus in subjects with post-traumatic stress disorder: a proton magnetic resonance spectroscopy study," European Journal of Neuroscience, 2007, vol. 25, pp. 324-329.

Meyerhoff, D. et al. "Cortical Gamma-Aminobutyric Acid and Glutamate in Posttraumatic Stress Disorder and Their Relationships to Self-Reported Sleep Quality," 2014, Sleep, vol. 37, No. 5, pp. 893-900.

Schmidt, U. et al. "Biomarkers in Posttraumatic Stress Disorder: Overview and Implications for Future Research," Hindawi Publishing Corporation Disease Markers, 2013, vol. 35 (1), pp. 43-54.

Quadrelli, S. et al. "Systematic review of in-vivo neuro magnetic resonance spectroscopy for the assessment of posttraumatic stress disorder." Psychiatry Research: Neuroimaging, 2018, vol. 282, pp. 110-125.

Henigsberg, N. et al. "Changes in Brain Metabolites Measured with Magnetic Resonance Spectroscopy in Antidepressant Responders with Comorbid Major Depression and Posttraumatic Stress Disorder." Collegium Antropologicum, 2011, vol. 35, Suppl. (1), pp. 145-148.

Yang, Z-Y. et al. "Proton magnetic resonance spectroscopy revealed differences in the glutamate + glutamine/creatine ratio of the anterior cingulate cortex between healthy and pediatric post-traumatic stress disorder patients diagnosed after 2008 Wenchuan earthquake," Psychiatry and Clinical Neurosciences, 2015, vol. 69, pp. 782-790.

* cited by examiner

SYSTEM AND METHOD FOR TREATING AND MONITORING POST TRAUMATIC STRESS DISORDER (PTSD)

CROSS-REFERENCE TO RELATED APPLICATIONS

The present application claims priority on U.S. Provisional Application Ser. No. 62/806,400 filed Feb. 15, 2019, which is incorporated by reference herein.

BACKGROUND OF THE INVENTION

The present invention relates to monitoring the treatment of patients with post-traumatic stress disorder (PTSD) and for monitoring the effects of the treatment.

PTSD is a condition widely experienced by patients, particularly members of the armed forces who are exposed to combat situations, and even military training short of actual combat situations. The treatment of PTSD may include one or more in a combination of periodical repetitive transcranial magnetic stimulation (rTMS), varying forms of regular psychotherapies such as Cognitive Behavioral Therapy (CBT), Behavioral Therapy (BT), Cognitive Processing Therapy (CPT), Eye Movement Desensitization Reprocessing (EMDR), narrative therapy, trauma focused therapy, and treatment with pharmaceuticals such as antidepressants and antipsychotics.

The evidence of the efficacy of these treatments is variable and often patients end up on multiple pharmaceuticals plus/minus the psychotherapies listed above. There is also evidence of significant rates of relapse with many patients developing chronic PTSD and life-long psycho-social impairment. As such, treatment and therapy for such patients is complex, and, an objective way to monitor such treatments is in great demand.

The following publications are incorporated by reference herein:

Quadrelli, Scott, et al. "Post-traumatic stress disorder affects fucose-α (1-2)-glycans in the human brain: preliminary findings of neuro deregulation using in vivo two-dimensional neuro MR spectroscopy." *Translational psychiatry* 9.1 (2019): 1-9.

Tosh, Nathan, et al. "Two New Fucose-α (1-2)-Glycans Assigned In The Healthy Human Brain Taking The Number To Seven." *Scientific Reports* (2019) 9:18806.

SUMMARY OF THE INVENTION

The present invention provides a method and system for monitoring patients with PTSD and the capacity to detect and report on the effect and progress of treatment and therapy. The technology was developed by monitoring the response to one or both of rTMS and psychotherapies such as EMDR on a periodic basis. However, the technique of monitoring therapeutic intervention applies to all type of therapies used to treat PTSD.

DETAILED DESCRIPTION OF THE PREFERRED EMBODIMENT

Figure 1:
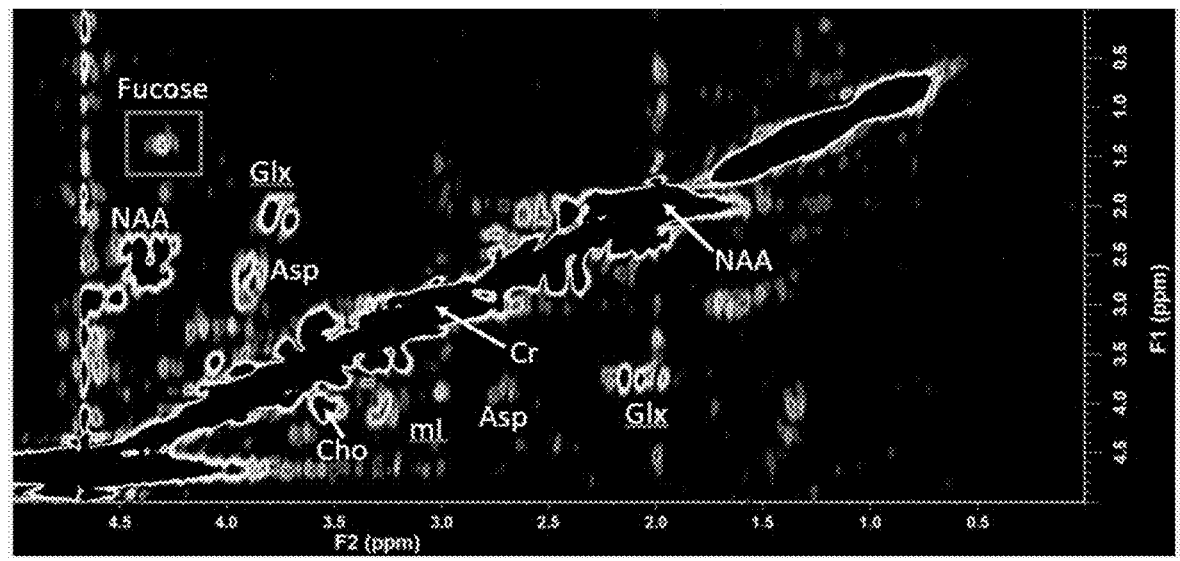
FIG. 1 is a plot of 2D-L-COSY (Two-Dimensional Correlated Spectroscopy) results from a patient with PTSD on a first visit before treatment.
Figure 2:
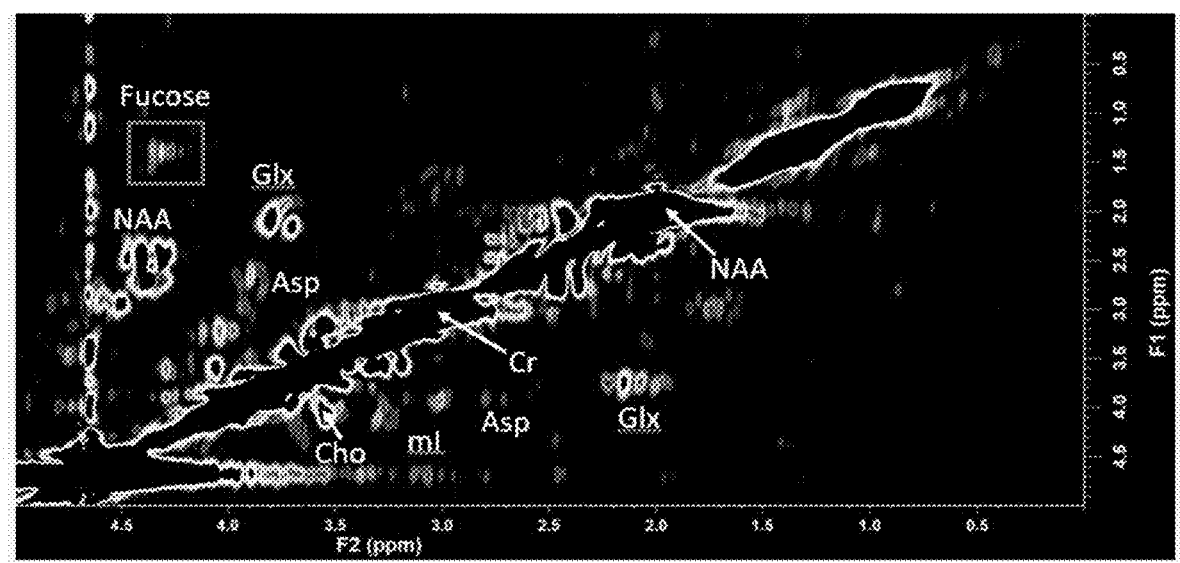
FIG. 2 is a plot of 2D L-COSY results from the same patient as in FIG. 1 on a second visit after 20 sessions of treatment of TMS and EMDR over a two week period.
Figure 3:
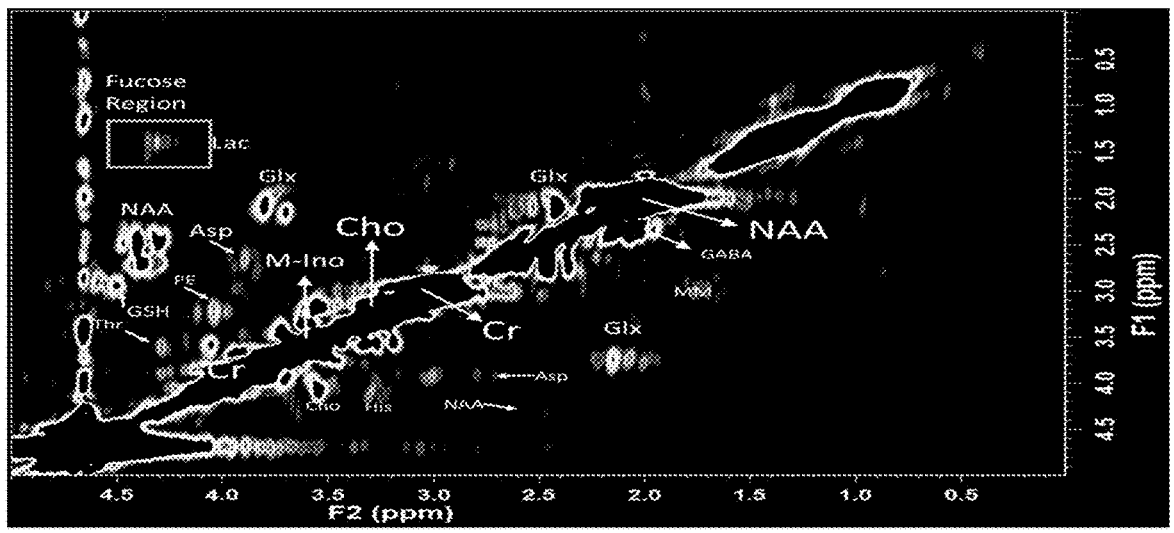
FIG. 3 is a plot of 2D L-COSY results from the same patient as in FIGS. 1 and 2 on a third visit 12 weeks after the second visit.
Figure 4:
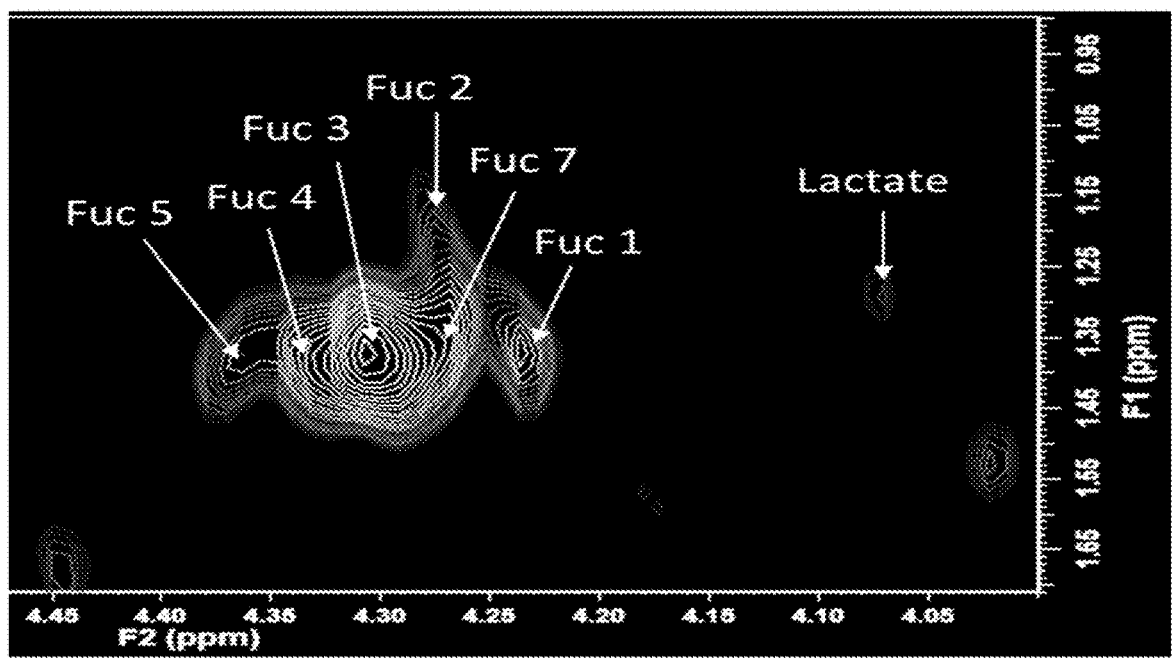
FIG. 4 is a 2D L-COSY plot of the fucose region (F2: 4-4.6 ppm) on the first visit before therapy, wherein the overall level of fucosylated glycans are very low; which shows a returning to normal signature but with substrate fucose visible.
Figure 5:
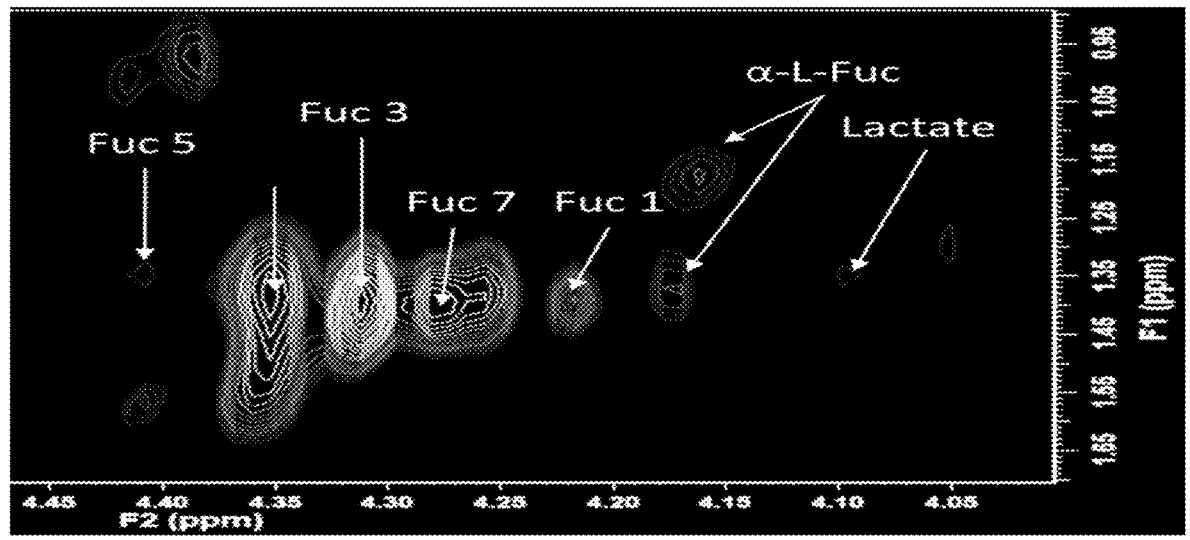
FIG. 5 is a 2D L-COSY plot of the fucose region (F2: 4-4.6 ppm) on the second visit after therapy, wherein the fucosylated glycans show a returning to normal signature but with substrate fucose visible.
Figure 6:
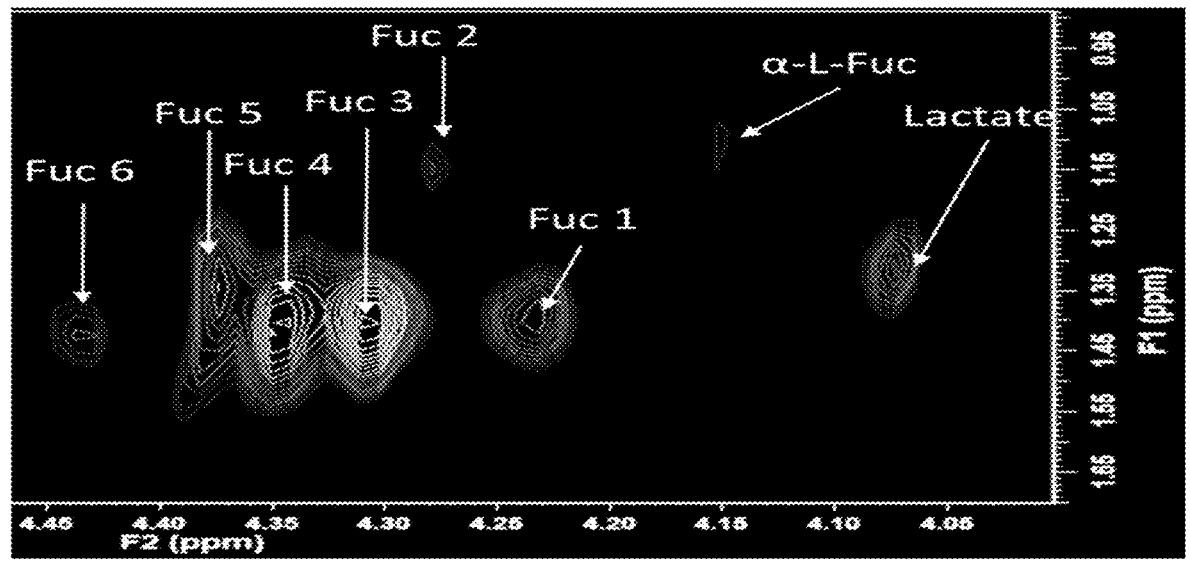
FIG. 6 is a 2D L-COSY plot of the fucose region (F2: 4-4.6 ppm) on the third visit, 12 weeks after therapy, wherein the fucosylated glycans show a returning to normal signature but with decreased free substrate fucose visible.
Figure 7:
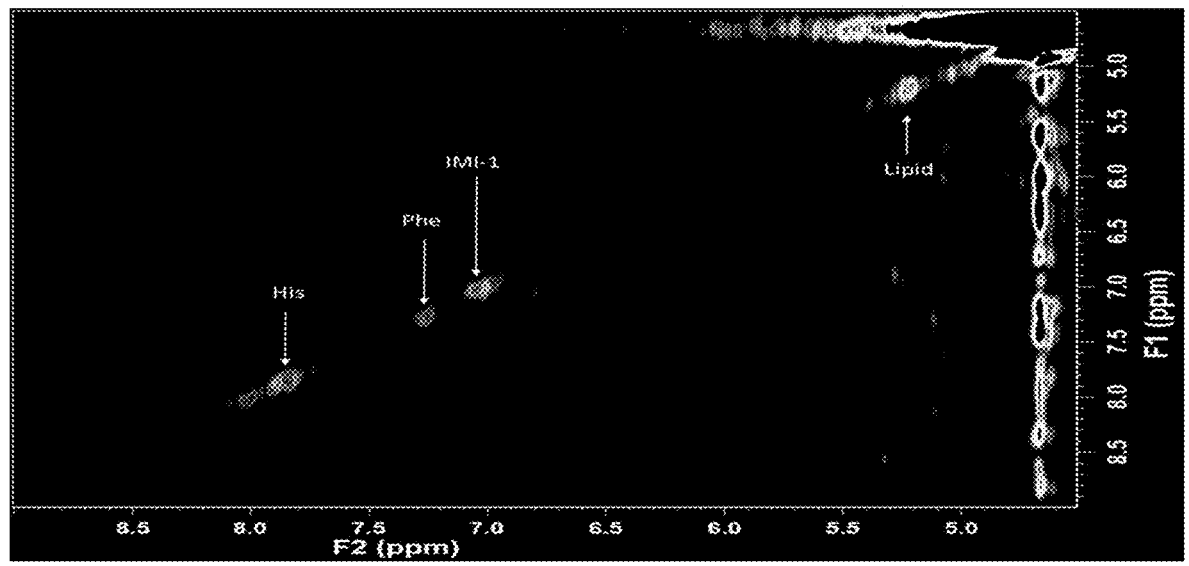
FIG. 7 is a plot of 2D L-COSY high field end of the spectrum of the same patient before therapy, wherein the plot shows lipid, imidazole, phenylalanine and histidine resonances with typical PTSD signature.
Figure 8:
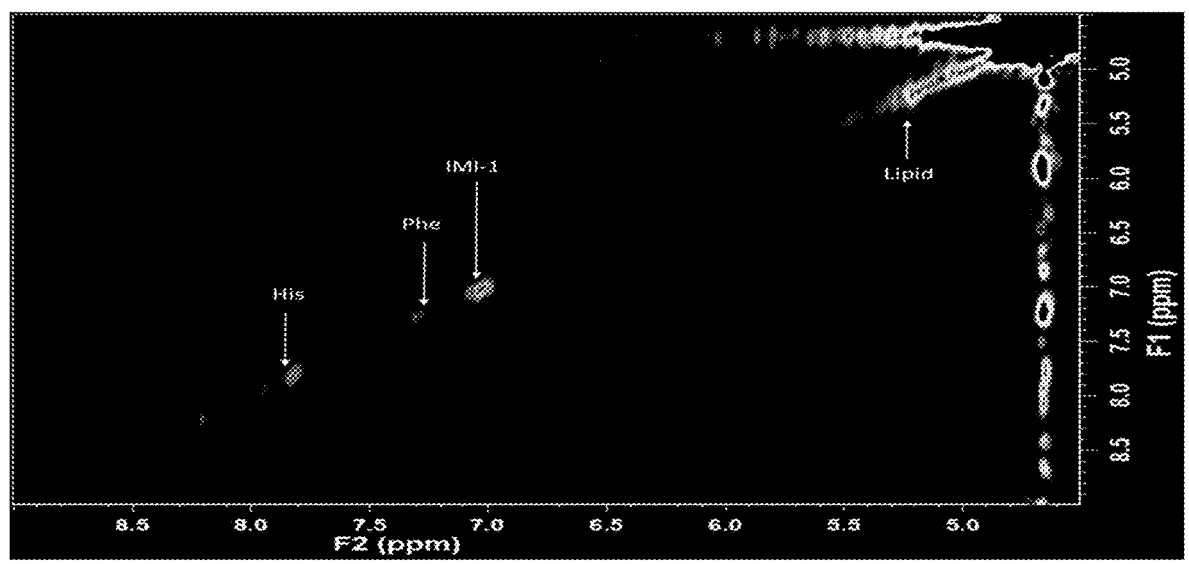
FIG. 8 is a plot of 2D L-COSY high field end of the spectrum of the same patient after therapy, wherein the plot shows decreased levels on neurochemicals in this region compared with before therapy which is comparable to a healthy signature.
Figure 9:
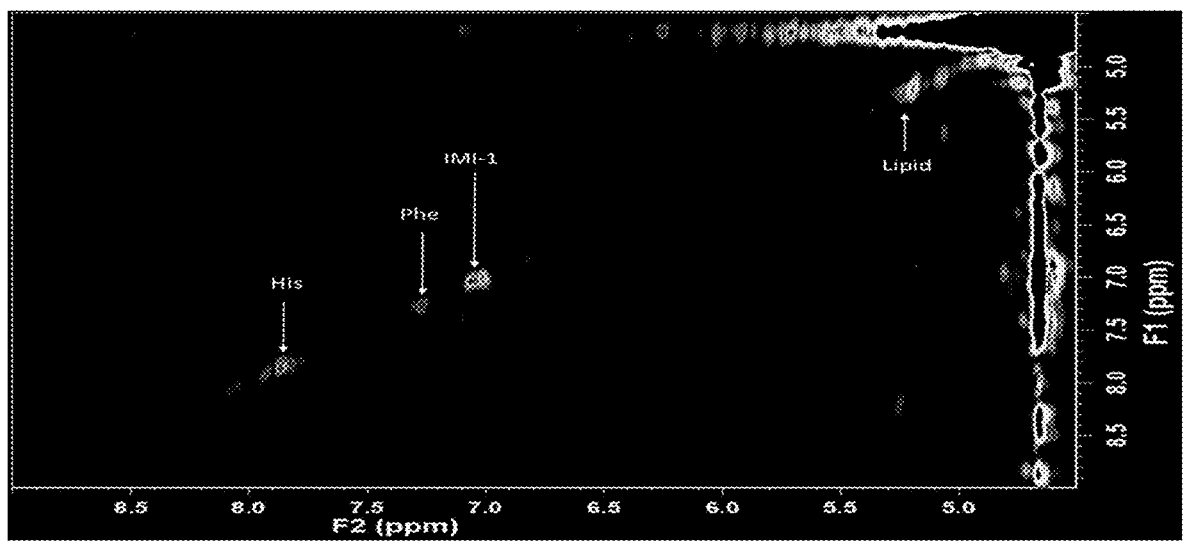
FIG. 9 is a plot of 2D L-COSY high field end of the spectrum of the same patient 12 weeks after therapy wherein the resonances in this region appear to be reverting to appear like the pre-therapy signature.

An embodiment of the invention will be described, but the invention is not limited to this embodiment.

The invention provides a method of monitoring therapeutic interventions for treating a patient with PTSD by: using a scanner to obtain pre-treatment neural spectroscopic data of at least one neuromarker chemical in the brain of the patient before treatment, treating the patient with at least one treatment protocol, after treatment, using the scanner to obtain post-treatment neural spectroscopic data of the at least one neuromarker chemical in the brain of the patient, and using a comparator to compare the results of the pre-treatment and post-treatment data to enable a determination of the effectiveness of the treatment.

The patient may be treated with rTMS, or a psychotherapy. The psychotherapy may be EMDR. The patient may be treated with a combination of at least two of rTMS, psychotherapies and pharmaceutical interventions. The method may further include the step of obtaining mid-treatment neural spectroscopic data during the treatment protocol, and comparing the mid-treatment data with the pre-treatment data. The at least one neurochemical marker may be at least one of Fucosylated glycans and free fucose substrate, GSH, Histidine, Lipid =C=, Glx, NAA (multiple resonances), Aspartate, GABA, Lactate, Phenylalanine, and PE-Histidine. The method may include a continuation of the treatment protocol continues, and obtaining post-treatment neural spectroscopic data repeatedly to monitor the patient's neurochemical profile to ensure no dysregulation of neurochemical markers are seen that could enable detection of the patient returning to an unhealthy state.

The steps of obtaining neural spectroscopic data may comprise obtaining the data using 2D COSY.

The invention provides a system for monitoring therapeutic interventions for treating a patient with PTSD, comprising: a scanner to obtain pre-treatment neural spectroscopic data of at least one neuromarker chemical in the brain of the patient before any treatment protocol, and after treatment of the patient with at least one treatment protocol, to obtain post-treatment neural spectroscopic data of the at least one neuromarker chemical in the brain, and a comparator for comparing the results of the pre-treatment and post-treatment data to enable a determination of the effectiveness of the treatment. The patient may be treated with rTMS, or a psychotherapy. The psychotherapy may be EMDR. The patient may be treated with a combination of at least two of rTMS, psychotherapies and pharmaceutical interventions. The scanner may obtain mid-treatment neural spectroscopic data during the treatment protocol. The scanner may obtain neural spectroscopic data of a neurochemical marker which is at least one of Fucosylated glycans and free fucose substrate, GSH, Histidine, Lipid =C=, Glx, NAA (multiple resonances), Aspartate, GABA, Lactate, Phenylalanine, and PE-Histidine. The scanner may continue to obtain spectroscopic data to monitor the patient's neurochemical profile to ensure no dysregulation of neurochemical markers are seen that could enable detection of the subject returning to an unhealthy state. The scanner may obtain neural spectroscopic data using 2D COSY.

Monitoring Treatment of PTSD Patient

A combat engineer officer with minimal blast exposure or head injury, but with a diagnosis of chronic PTSD, a history of Major Depressive Disorder (MDD) (not currently diagnosed), chronic suicidality/self-harm behavior, was treated with a combination of rTMS and EMDR on a daily basis for 2 weeks.

The rTMS treatment involved placement of an electromagnetic coil against the scalp near the forehead, and delivering magnetic pulses to stimulate the nerve cells of the patient's brain. It is believed that the effects of high-frequency rTMS in depression occur through an increase of activity in the left dorsolateral prefrontal cortex (DLPFC), which is proposed to be underactive in patients with depression. Low-frequency right-sided rTMS is proposed to reduce right-sided DLPFC activity which is proposed to be overactive in patients with depression. The EMDR treatment involved 8 phases of trauma-informed intervention that commenced with stabilization, exposure work with the use of eye movement, with the focus of reintegration into varying social/professional/personal roles. Each EMDR session was conducted in concurrently with rTMS.

The Figs. show 2D L-COSY results at the first scan before any treatment, at the second scan after intensive rTMS and EMDR sessions over a period of two weeks, and at follow up scan 12 weeks later. As can be seen the results after TMS and EMDR treatment show a reaction to the therapy, with significant neurochemical changes. Before the intensive therapy, the patient's neurochemical magnetic resonance spectroscopy (MRS) spectrum was significantly different to a healthy neurochemical profile. After the treatment, the neurochemical profile changed and appeared more indicative of a healthy neurochemical profile. At a follow up 12 weeks later there was evidence of repopulation of the glycans that was different to either of the first and second scans. Within the fucose region of the MRS spectrum, an area of particular interest in PTSD, there was evidence or repopulation of fucosylated glycans and a return towards healthy brain signature and a potential regression at a later time point.

Method of Acquiring Data

Data were acquired on a 60 cm bore, 3T Prisma scanner (Siemens, Erlangen, Germany, software version VD13D or VE11C) with a 64-channel head and neck coil (Siemens, Erlangen).

Structural Imaging

For anatomical morphometry and voxel placement, a three-dimensional Ti weighted MPRAGE was acquired (TR/TE=2530/1.7 ms, 120 flip angle, FOV=256×256 mm, voxel size 1 mm3, NEX 4, IPAT=3, acquisition time=4 mins), and reconstructed in all planes for accurate MRS voxel placement.

Two-Dimensional L-COSY Parameters

2D L-COSY data were acquired from a 3×3×3 cm voxel located in the Posterior Cingulate Gyms (PCG). The carrier frequency was set at 2.4 ppm, TR 1.5 s; water suppression using WET; spectral width of 2000 Hz; increment size of 0.8 ms in 96 Ti increments (giving an indirect spectral width of 1250 Hz); 8 averages per increment and 1024 data points. Acquisition time was 19 minutes. Shimming adjustments were undertaken on each scan by invalidating the automatic BO field mapping technique supplied by the vendor. The automatic shim process was then performed followed by the manual adjustment of the shim gradients in the X, Y and Z directions to achieve a full width half maximum (FWHM) of the water peak between 12-15 Hz.

2D L-COSY Data Analysis

Raw data were pre-processed in Matlab 18. The signal was combined from multiple channels, rows concatenated into a 2D matrix and reformatted. The resulting file was transformed in 2D using FelixNMR, a specialised 2D NMR processing software. The post-processing parameters used in Felix were: F2 domain (skewed sine-squared window, zero-filling to 2048 points, magnitude mode), F1 domain (sine-squared window, linear prediction to 96 points, zero-filling to 512 points, magnitude mode). In Felix, each prominent diagonal and cross peak was selected and integrated to determine the peak chemical shift, intensity, and volume. These values were internally referenced using the total creatine methyl diagonal peak at 3.02 ppm. Peak and cross-speak assignments were manually adjusted, to ensure the region of integration was centered on the peak, then exported for further analysis.

The following Table shows the size of the statistically significant changes in various neuro-chemical markers at a pre-treatment time, and a post-treatment time, and a follow up 12 weeks after therapy, along with the percentage change, positive or negative. Also included are average healthy control and PTSD signatures for reference. Significant different neurochemical values at each time point are shaded.

| Neuro-chemical | Average Healthy Control | Pre-therapy % Change | Post-therapy % Change | 12 weeks post-therapy % Change | Average PTSD |
|---|---|---|---|---|---|
| Glx_lower | 0.091 ± 0.008 | −12% | −27% | −16% | 0.095 ± 0.021 |
| Lipid | 0.079 ± 0.006 | −3% | −21% | −16% | 0.086 ± 0.046 |
| NAA_4 | 0.080 ± 0.008 | 4% | −17% | −11% | 0.078 ± 0.012 |
| NAA_2 | 0.112 ± 0.013 | −10% | −24% | −19% | 0.115 ± 0.034 |
| GSH_2 | 0.011 ± 0.002 | −4% | −7% | −51% | 0.011 ± 0.002 |
| NAA_3 | 0.322 ± 0.028 | −5% | −20% | −13% | 0.315 ± 0.045 |
| Asp | 0.013 ± 0.003 | −10% | −40% | −25% | 0.013 ± 0.003 |
| Hist | 0.019 ± 0.007 | −10% | −39% | −8% | 0.018 ± 0.006 |
| Asp_1 | 0.055 ± 0.009 | −0.2% | −39% | −12% | 0.054 ± 0.007 |
| GABA | 0.007 ± 0.002 | −43% | −19% | −4% | 0.008 ± 0.004 |
| PE–Hist | 0.051 ± 0.006 | 1% | −19% | −5% | 0.062 ± 0.026 |
| Fuc_5 | 0.006 ± 0.002 | −53% | −50% | −24% | 0.007 ± 0.003 |
| Fuc_7 | 0.006 ± 0.001 | 7% | −23% | −45% | 0.006 ± 0.002 |
| Lactate | 0.006 ± 0.002 | −52% | −34% | −17% | 0.006 ± 0.003 |
| Lipid_3 | 0.023 ± 0.005 | 46% | 73% | 31% | 0.030 ± 0.017 |
| Phe | 0.015 ± 0.002 | 0.4% | −25% | −10% | 0.015 ± 0.002 |
| Hist_1 | 0.045 ± 0.005 | −3% | −24% | −13% | 0.045 ± 0.006 |

In summary, the results of the method according to the invention show that TMS and EMDR treatment of a patient with PTSD was successful, which matched with the patients self-reported symptoms. These results give evidence that the effects of the treatment can be monitored quantitatively and objectively with a 2D COSY. The changes in certain neurochemicals seen using 2D COSY following therapy showed significant re-regulation compared to pre-treatment neurochemical levels, which can be quantifiably measured. The same results could be obtained using 1D data which is not obtained from 2D COSY.

Figure 10:
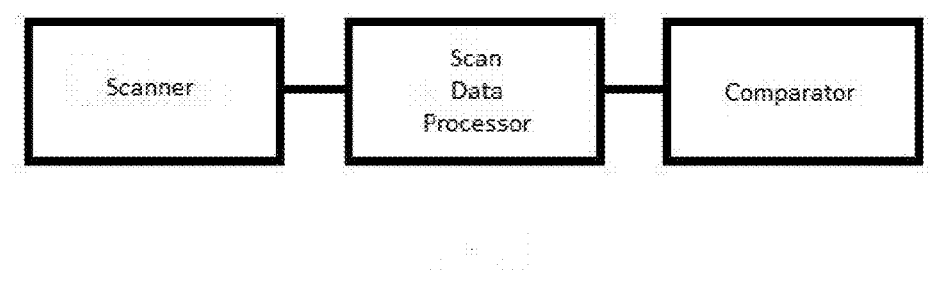
FIG. 10 is a block diagram of a system which may be used to practice the invention.

The neuromarker chemicals that can be monitored for re-regulation include
a. Fucosylated glycans and free fucose substrate
b. GSH
c. Histidine
d. Lipid =C=
e. Glx
f. NAA (multiple resonances)
g. Aspartate and Aspartate 1
h. GABA
i. Lactate
j. Phenylalanine
k. PE-Histidine FIG. 10 shows a block diagram of a system which can be used to obtain and analyze the data, and compare the data with reference data from healthy controls. The system includes a scanner for obtaining the data from a subject using the acquisition parameters described above, a data processor for processing the data as described above, and a comparator for comparing the processed data for the selected neurochemicals to those for healthy controls, to determine the subject's responsiveness to treatment.

Figure 11:
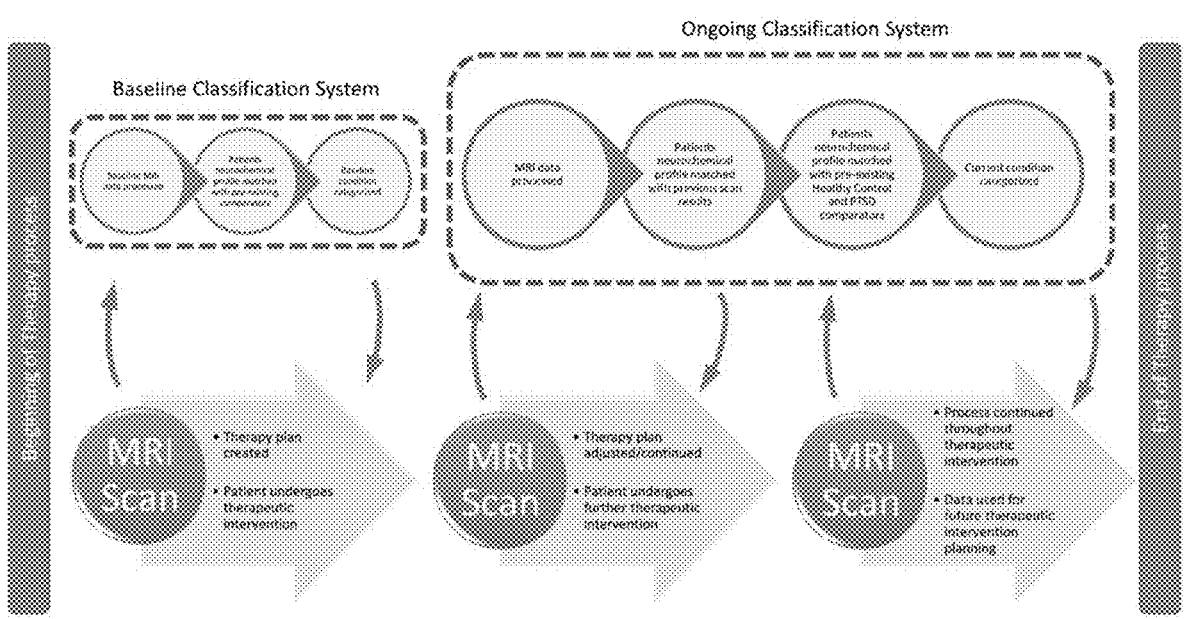
FIG. 11 is a flow chart showing steps of the method according to a preferred embodiment.

FIG. 11 shows a flow chart of method steps according to a preferred embodiment, the sequence going from left to right. At the beginning of the treatment process, as shown on the left, an MRI scan is performed to obtain a baseline, the baseline MRI data is processed, the patient's neurochemical profile is matched with pre-existing comparators, and a baseline condition of the patient is categorized. A therapy plan is created, and the patient undergoes therapeutic intervention.

During the therapy process, the patient undergoes an MRI scan, wherein the MRI data is processed, the patent's neurochemical profile is compared/matched with previous scan results, the patient's neurochemical profile is compared/matched with pre-existing healthy control and PTSD comparators, and the patient's current condition is categorized/determined. This mid-treatment assessment could be repeated several times during the treatment process. When the results of one of the MRI scans and data processing indicate that the patient has been treated sufficiently, or a determination is made that the patient will not receive any further treatment for one reason or another, the treatment terminates, and the MRI data is used for possible feature therapeutic intervention planning.

Although one embodiment of the invention has been described, the invention is not limited to this embodiment. For example, neurochemicals other than those listed herein may be effective in monitoring the existence of PTSD and recovery from treatment. While the embodiment described used a combination of rTMS and EMDR this method of monitoring treatment applies to all combinations of rTMS, psychotherapies and pharmaceutical interventions.

What is claimed is:

1. A method of monitoring therapeutic interventions for treating a patient with PTSD by:
    using a scanner to obtain pre-treatment neural spectroscopic data of at least one neuromarker chemical in a brain of the patient before treatment, the at least one neuromarker chemical being at least one of Fuc 7, and PE-Histidine, using a comparator to compare the pre-treatment neural spectroscopic data with neural spectroscopic data of a healthy profile, treating the patient with at least one treatment protocol, after the at least one treatment protocol is performed on the patient, using the scanner to obtain post-treatment neural spectroscopic data of the at least one neuromarker chemical in the brain of the patient, and using the comparator to compare the pre-treatment and post-treatment neural spectroscopic data.

2. The method of claim 1 wherein the patient is treated with rTMS.

3. The method of claim 1, wherein the patient is treated with a psychotherapy.

4. The method of claim 3, wherein the psychotherapy is EMDR.

5. The method of claim 1, wherein the patient is treated with a combination of at least two of rTMS, psychotherapies and pharmaceutical interventions.

6. The method of claim 1, further including the step of obtaining mid-treatment neural spectroscopic data during the at least one treatment protocol, and comparing the mid-treatment data with the pre-treatment data.

7. The method of claim 1, wherein the at least one treatment protocol continues, and obtaining post-treatment neural spectroscopic data is repeated to monitor the patient's post-treatment neural spectroscopic data.

8. The method of claim 1, wherein the steps of obtaining neural spectroscopic data comprise obtaining the data using 2D COSY.

9. A system for monitoring therapeutic interventions for treating a patient with PTSD, comprising:
a scanner to obtain pre-treatment neural spectroscopic data of at least one neuromarker chemical in a brain of the patient before any treatment protocol, and after at least one treatment protocol is performed on the patient, to obtain post-treatment neural spectroscopic data of the at least one neuromarker chemical in the brain, and a comparator for comparing the pre-treatment and post-treatment data to enable a determination of whether the treatment protocol was effective at improving PTSD, wherein the neuromarker chemical is at least one of Fuc 7, and PE-Histidine.

10. The system of claim 9, wherein the treatment protocol is rTMS.

11. The system of claim 9, wherein the treatment protocol is a psychotherapy.

12. The system of claim 11, wherein the psychotherapy is EMDR.

13. The system of claim 9, wherein the treatment protocol is a combination of at least two of rTMS, psychotherapies and pharmaceutical interventions.

14. The system of claim 9, wherein the scanner obtains mid-treatment neural spectroscopic data during the at least one treatment protocol.

15. The system of claim 9, wherein the scanner continues to obtain spectroscopic data to monitor a neurochemical profile of the patient to ensure no dysregulation of neurochemical markers are seen that could enable detection of the patient returning to an unhealthy state.

16. The system of claim 9, wherein the scanner obtains pre-treatment and post-treatment neural spectroscopic data using 2D COSY.

17. A method of monitoring therapeutic interventions for treating a patient with PTSD by:
using a scanner to obtain pre-treatment neural spectroscopic data of at least one neuromarker chemical in a brain of the patient before at least one treatment protocol, the at least one neuromarker chemical being at least one of Fuc 7, and PE-Histidine, treating the patient with at least one treatment protocol; after at least one treatment protocol, using the scanner to obtain post-treatment neural spectroscopic data of the at least one neuromarker chemical in the brain of the patient, and using a comparator to compare the pre-treatment and post-treatment neural spectroscopic data to enable a determination of whether the treatment protocol was effective at treating PTSD.

18. A method of obtaining a pre-treatment condition of a patient for PTSD, comprising:
using a scanner to obtain pre-treatment neural spectroscopic data of at least one neuromarker chemical in a brain of the patient, the at least one neuromarker being at least one of Fuc 7, and PE-Histidine, and
using a comparator to compare the pre-treatment neural spectroscopic data with neural spectroscopic data of a healthy profile to determine a pre-treatment baseline condition of the patient.

19. A system for obtaining a pre-treatment condition of a patient for PTSD, comprising:
a scanner to obtain pre-treatment neural spectroscopic data of at least one neuromarker chemical in a brain of the patient before treatment, the at least one neuromarker chemical being at least one of Fuc 7, and PE-Histidine; and
a comparator to compare the pre-treatment neural spectroscopic data with neural spectroscopic data of a healthy profile.

* * * * *